(12) United States Patent
Villa et al.

(10) Patent No.: US 8,586,351 B2
(45) Date of Patent: *Nov. 19, 2013

(54) ELECTRONIC DETECTION OF BIOLOGICAL MATERIALS

(75) Inventors: Flavio Francesco Villa, Milan (IT); Ubaldo Mastromatteo, Bareggio (IT); Gabriele Barlocchi, Cornaredo (IT)

(73) Assignee: STMicroelectronics S.r.l. (IT)

( * ) Notice: Subject to any disclaimer, the term of this patent is extended or adjusted under 35 U.S.C. 154(b) by 621 days.

This patent is subject to a terminal disclaimer.

(21) Appl. No.: 12/649,019

(22) Filed: Dec. 29, 2009

(65) Prior Publication Data

US 2010/0163410 A1    Jul. 1, 2010

(30) Foreign Application Priority Data

Dec. 30, 2008  (IT) ............................... TO2008A1013

(51) Int. Cl.
*C12M 1/34* (2006.01)

(52) U.S. Cl.
USPC ...... 435/287.2; 435/6.12; 204/400; 73/24.01; 156/247

(58) Field of Classification Search
USPC ......... 435/287.2, 6.12; 204/400; 156/60, 247; 73/23, 34, 24.01, 24.06, 661; 205/777.5
See application file for complete search history.

(56) References Cited

U.S. PATENT DOCUMENTS

| | | | |
|---|---|---|---|
| 5,945,280 A | | 8/1999 | Fawcett et al. |
| 6,054,277 A | * | 4/2000 | Furcht et al. ................. 435/6.11 |
| 6,448,695 B2 | | 9/2002 | Milsom |
| 6,787,052 B1 | * | 9/2004 | Vaganov ......................... 216/57 |
| 6,812,619 B1 | | 11/2004 | Kaitila et al. |
| 6,933,807 B2 | | 8/2005 | Marksteiner et al. |
| 2004/0023236 A1 | * | 2/2004 | Potter et al. ....................... 435/6 |
| 2004/0086427 A1 | * | 5/2004 | Childers et al. ............... 422/100 |
| 2004/0185592 A1 | | 9/2004 | Bergaud et al. |
| 2006/0125489 A1 | * | 6/2006 | Feucht et al. .................. 324/633 |
| 2006/0223167 A1 | * | 10/2006 | Chaton et al. ............. 435/287.2 |

FOREIGN PATENT DOCUMENTS

| | | |
|---|---|---|
| EP | 1577656 | 9/2005 |
| IT | RM2001A000455 | 1/2003 |

OTHER PUBLICATIONS

Nicu, L., et al., Resonating piezoelectric membranes for microelectromechanically based bioassay: detection of streptavidin-gold nanoparticles interaction with biotinylated DNA. Sensors and Actuators B 110: 125-136 (2005).

M. Benetti, et al., Chemical Sensor Based on Thin Film Bulk Acoustic Wave Resonator (TFBAR). Symposium: Sensors and Microsystems, Feb. 15-17, 2005, Firenze, Italy.

Joel F. Rosenbaum, Bulk Acoustic Wave Theory and Devices, Section 11.7: Composite Resonators. Artech House Inc., Norwood, MA, 1988.

Cyrano "Nose" the smell of success. NASA Spinoff 2001 (http://www.sti.nasa.gov/tto//spinoff2001/ps4.html).

* cited by examiner

*Primary Examiner* — Michael Hobbs

(74) *Attorney, Agent, or Firm* — Boulware & Valoir

(57) ABSTRACT

A hybridization detecting device, wherein a probe cell has a body of semiconductor material forming a diaphragm, a first electrode on the diaphragm, a piezoelectric region on the first electrode, a second electrode on the piezoelectric region and a detection layer on the second electrode. The body accommodates a buried cavity downwardly delimiting the diaphragm.

20 Claims, 7 Drawing Sheets

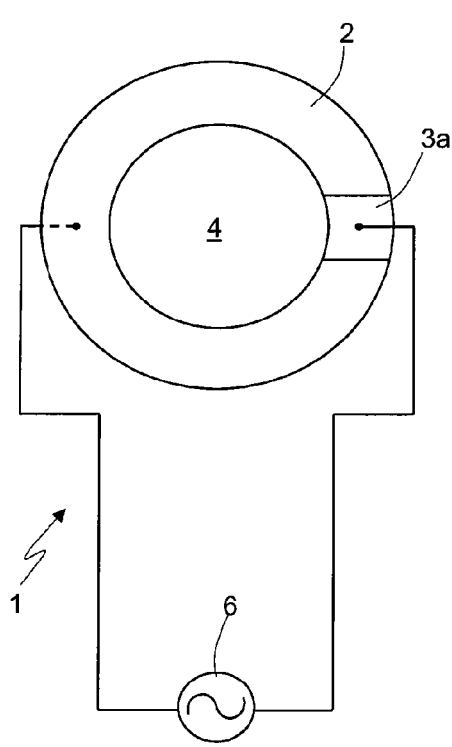
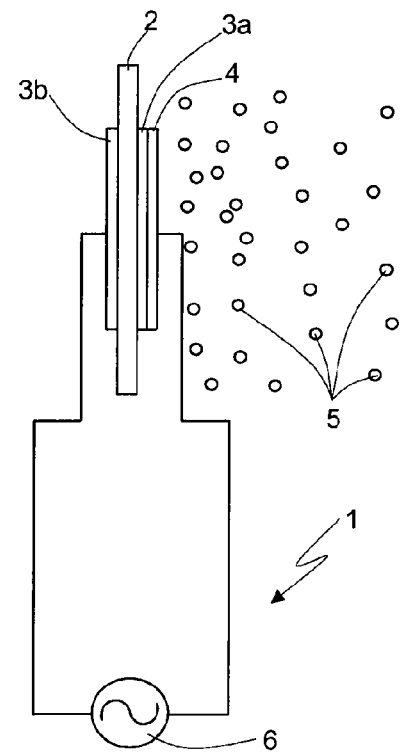
Fig. 1a (Prior Art)  Fig. 1b (Prior Art)
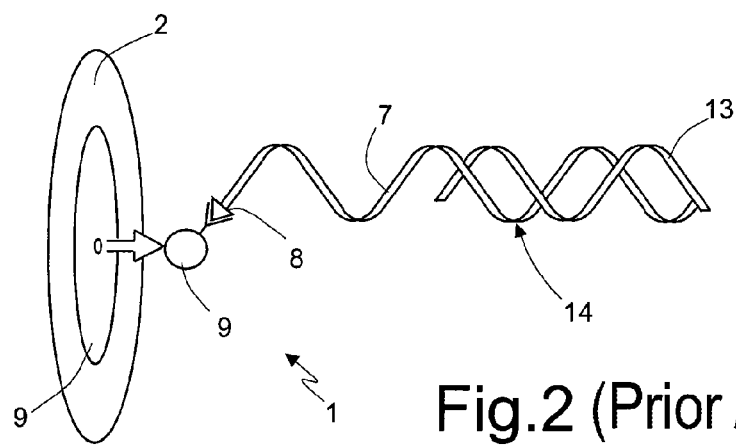
Fig. 2 (Prior Art)

ELECTRONIC DETECTION OF BIOLOGICAL MATERIALS

CROSS-REFERENCE TO RELATED APPLICATIONS

This application claims priority to Italian Application No. TO2008A001013, filed Dec. 30, 2008, incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The present invention relates to a device for electronic detection of biological materials, such as nucleic acids, proteins, lipids, carbohydrates and the like.

BACKGROUND OF THE INVENTION

As is known, the identification of specific biological materials sequences is of significance in many areas including clinical, environmental and food microbiology diagnosis. In particular, the analysis of gene sequences plays a fundamental role in rapid detection of genetic mutations and infectious organisms. This means it is possible to make reliable diagnosis of diseases even before any symptoms appear.

Typical procedures for analyzing biological materials, such as nucleic acid, protein, lipid, carbohydrate, and other biological molecules, involve a variety of operations starting from raw material. These operations may include various degrees of cell separation or purification, lysis, amplification or purification, and analysis of the resulting amplification or purification product.

As an example, in DNA-based blood analyses samples are often purified by filtration, centrifugation or by electrophoresis so as to eliminate all the non-nucleated cells, which are generally not useful for DNA analysis. Then, the remaining white blood cells are broken up or lysed using chemical, thermal or biochemical means in order to liberate the DNA to be analyzed. Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

If RNA is to be analyzed, the procedures are similar, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof. A common analysis technique is an analysis by hybridization, wherein the amplified DNA is passed over a plurality of detectors made up of individual oligonucleotide detector fragments that are anchored on suitable substrates. The individual oligonucleotide detector fragments or "probes" may be complementary to the target amplified DNA strands. If the amplified DNA strands are complementary to the probes, stable bonds are formed between them (hybridization). The presence of a double stranded DNA in the mixture is thus indicative of a match and hybridization serves as a sequence detection mechanism.

In standard microarrays, the probes are attached to a solid surface (glass or silicon) using a linker molecule. Probe-target hybridization is usually detected and quantified by fluorescence-based detection. The hybridized detectors can be read using a wide variety of means, including optical, electromagnetic, electromechanical or thermal means.

Fluorescence-based detection, however, has several significant drawbacks, since: 1) it requires previous manipulation of the analyte to introduce the optical markers; 2) it requires expensive instrumentation for optical reading. Typical commercial equipments are systems with photomultiplier tubes (PMTs) or charge-coupled devices (CCDs), which consume high power and cannot be easily integrated with electronic circuits in an inexpensive way; and 3) its sensitivity may be limited by any lack of homogeneity in the marker distribution.

Recently, the use of quartz crystal microbalance (QCM) for hybridization detection has been proposed, which avoids the need for radioisotopes or fluorophores. Quartz is one member of a family of crystals that experience the piezoelectric effect (to generate an electric potential in response to applied mechanical stress), and the relationship between applied voltage and mechanical deformation is well known. A QCM measures a mass per unit area by measuring the change in frequency of a quartz crystal resonator, wherein the resonance is disturbed by the addition or removal of a small mass. The QCM can be used under vacuum, in gas phase, and more recently in liquid environments. In liquid, it is highly effective at determining the affinity of molecules to surfaces functionalized with recognition sites, and can be used to detect hybridization of nucleic acids, binding of peptides, and the like. Frequency measurements are easily made to high precision, thus it is easy to measure mass densities down to a level of below 1 μg/cm2.

FIGS. 1a and 1b show a quartz crystal microbalance 1 comprising a quartz disc 2 having gold electrodes 3a, 3b patterned on opposite sides of the quartz disc 2. One electrode 3a is covered by a sensing layer 4 capable of bonding with an analyte of interest (shown as dots 5 in FIG. 1b). The microbalance 1, connected in an oscillating circuit, fixes the oscillation frequency of the system at the natural frequency of the quartz disc 2.

By virtue of the hybridization, the mass of the quartz disc 2 increases and causes a variation in the oscillation frequency of the oscillating circuit, which can be easily measured.

FIG. 2 shows a quartz disc 2, functionalized by a biotinylated DNA probe layer having a high affinity with a previously deposited streptavidin layer. In particular, FIG. 2 shows a microbalance 1 wherein the sensing layer 4 comprises a plurality of single-strand DNA segments 7 functionalized by biotin 8; biotin 8 is bound to a streptavidin layer 9 deposited on the quartz disc 2. In the drawing, the single-strand DNA segment 7 is bound to a target strand 13, forming a double-strand 14.

The basic equation describing the relationship between the change in resonant frequency of an oscillating piezoelectric crystal and the mass deposited on the crystal surface was derived by Sauerbrey in 1959. Let A be the area of the quartz crystal in $cm^2$, $\Delta M$ the mass difference due to the hybridization in g, $f_0$ the rest resonance frequency of piezoelectric quartz crystal in MHz before hybridization, it can be obtained:

$$\Delta f = -2.26 \times 10^{-6} \frac{f_o^2}{A} \Delta m \quad (1)$$

The sensitivity S of the crystal sensor is given by:

$$S = \frac{\Delta f}{\Delta m} = -2.26 \times 10^{-6} \frac{f_o^2}{A} \quad (2)$$

Thus, for a given piezoelectric crystal, the sensitivity of a microbalance can be increased by reducing the dimensions of the electrode surface. Therefore, miniaturization (e.g., silicon integration) will allow the QCM to reach very high sensitivity, so as to be able to detect even very small mass variations.

Semiconductor piezoelectric sensors have been disclosed for a plurality of applications. In particular, bulk-integrated, acoustic wave sensors using piezoelectric layers are known, wherein a piezoelectric layer, sandwiched between two electrode layers, overlies a cavity and forms an acoustic resonator (see, e.g., "Bulk Acoustic Wave Theory and Devices" Joel F. Rosenbaum Artech House Inc, 1988).

These electro-acoustic resonators have been proposed for forming sensors of several types, such as force, pressure, acceleration, weight and chemicals sensors, all of which exploit the variation in the oscillation frequency of the acoustic resonator following a mass variation and/or its geometrical configuration.

Known sensors have cavities formed by bulk micromachining by etching silicon substrate from the back using tetramethylammoniumhydroxide (TMAH, see, e.g. "Sensors and Microsystems: Proceedings of the 10th Italian Conference" A. G. Mignani, R. Falciai, C. Di Natale, A. D'Amico, World Scientific Publishing Company, July 2008—pages 326-331). In particular, according to this known technique, a silicon nitride layer, acting as an etch stop, is deposited on a surface of a silicon substrate. Then a stack of a first aluminum layer (lower electrode), an aluminum nitride layer and a second aluminum layer (upper electrode) is deposited. The substrate is anisotropically etched from the back and the etching stops at the silicon nitride layer. The wafer is then diced. In each die so obtained, the stack forms a diaphragm, whereon a thin layer of a sensitive probe material, such as porphyrin, may be deposited.

This process is not usual in current production lines for integrated circuits.

In addition, this etching technique causes the formation of a cavity having a trapezoidal section, with a shorter base formed by the diaphragm and sloping sides at 40°-60°. Since the thickness of the substrate is generally about 675-700 µm, the longer base of the cavity is longer about 1.2-1.4 mm than the diaphragm. The total area needed for each microbalance is thus much higher than the area of the oscillating region alone. Therefore, the microbalance is, as a whole, cumbersome.

As a consequence, in general, known piezoelectric sensors do not have wide application.

Thus, an aim of the invention is to devise a detector of biological materials that can be easily integrated, has high sensitivity, low manufacturing costs and high reliability.

SUMMARY OF THE INVENTION

A hybridization detecting device comprises a body of semiconductor material integrating both a probe cell and an electronic high-frequency circuit, the probe having a body of semiconductor material forming a diaphragm, a first electrode on the diaphragm, a piezoelectric region on the first electrode, a second electrode on the piezoelectric region and a detection layer on the second electrode.

A process for manufacturing a hybridization detecting device comprises: providing a wafer of semiconductor material having a surface; integrating an electronic circuit in the wafer; forming a diaphragm laterally to the electronic circuit; forming a first electrode on the diaphragm; forming a piezoelectric region on the first electrode; forming a second electrode on the piezoelectric region; and forming a detection layer on the second electrode.

BRIEF DESCRIPTION OF THE DRAWINGS

For the understanding of the present invention, preferred embodiments thereof are now described, purely as a non-limitative example, with reference to the enclosed drawings, wherein:

FIGS. 1a, 1b are a front and a side elevation view of a known detector;

FIG. 2 is a top plan view of the detector of FIGS. 1a, 1b;

DESCRIPTION OF EMBODIMENTS OF THE INVENTION

Figure 3:
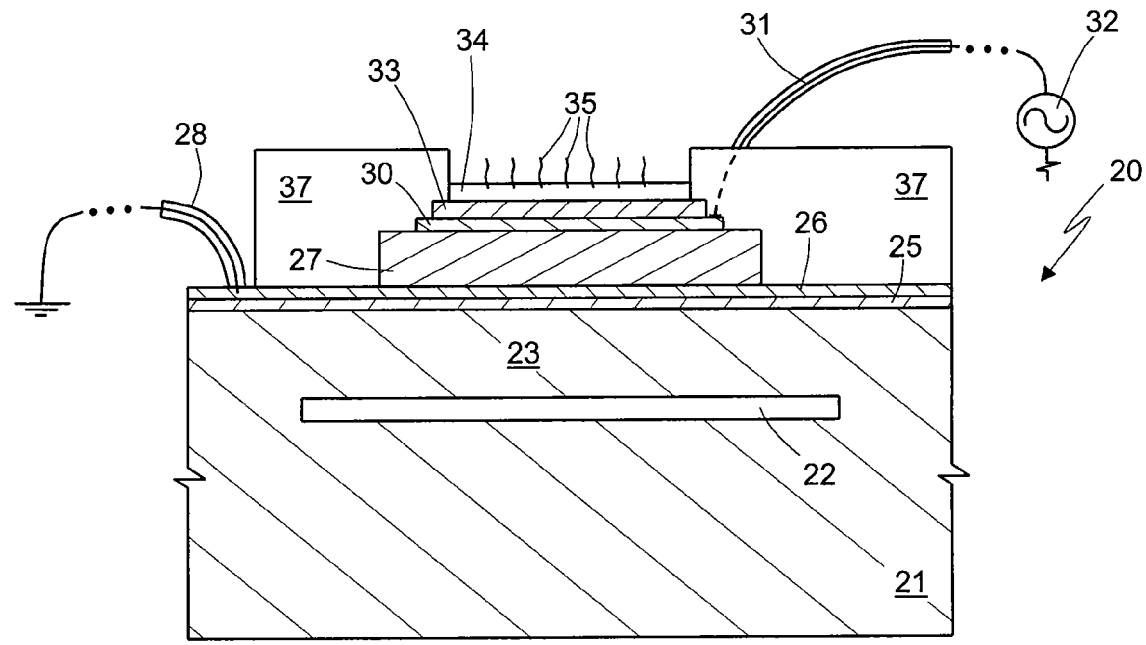
FIG. 3 is an enlarged, cross-sectional view of an embodiment of the instant detection device.

FIG. 3 shows a spot or probe cell 20 integrated on a body 21 of semiconductor material, e.g. monocrystalline silicon, which has a buried cavity 22 delimiting the bottom of diaphragm 23, also of monocrystalline silicon.

A buffer layer 25, for example of aluminum nitride (AlN), extends on the diaphragm 23 and a bottom electrode 26, for example of molybdenum, extends on the buffer layer 25. In this embodiment, buffer layer 25 may have a thickness of 30 to 100 nm, e.g. 50 nm, and bottom electrode 26 may have a thickness of 50 to 150 nm, e.g., 100 nm.

A piezoelectric region 27 extends on the bottom electrode 26 and has here a smaller area than the bottom electrode 26, to allow electrical connection of the bottom electrode 26 to ground, here through a shielded wire 28. Piezoelectric region 27 has a thickness of 0.5 to 3 µm, e.g. of about 1 µm, and a diameter of 100 to 300 µm.

An upper electrode 30, for example of molybdenum with a thickness of 50 to 150 nm, e.g. 100 nm, extends on the piezoelectric region 27. Upper electrode 30 may have the same or a smaller area than piezoelectric region 27 and is electrically connected, e.g. through a shielded wire 31, to an oscillator 32, of known type and thus not shown in detail.

A bond region 33, e.g. of NiPdAu, extends on the upper electrode 30 and is covered by a detecting layer 34, e.g. a biotinylated DNA probe layer including probe segments 35. A protection layer 37 extends on the surface of the probe cell 20, except at the sensing layer 34 and at the pads for the wires 28, 31. The protection layer is chosen to be suitable for the analyte being detected, and many passivating means are known in the art.

In the embodiment shown, the diaphragm 23, the piezoelectric region 27 and the overlaying regions 30, 33, 34 may have disc shape, but other shapes are also possible.

The presence of the diaphragm 23 under the piezoelectric region 27 allows the probe cell to operate at a frequency that can be easily processed by associated control circuitry implemented using standard manufacturing techniques. In the probe cell 20 of FIGS. 3 and 7, the diaphragm 23 operates as an oscillation damper, lowering the resonance frequency in the range of MHz. For example, with a diaphragm 23 having a thickness of 20 μm, piezoelectric region 27 having a thickness of 1 μm and layers 25, 26, 30 and 33 having a total thickness of about 400 nm, it is possible to obtain an oscillation frequency $f_0$ of about some hundreds of MHz, for example 200 MHz.

The operation of the probe cell 20 of FIG. 3 is as follows. The circuit formed by the piezoelectric region 27 and the oscillator 32 is an electronic resonator having its own oscillation frequency depending on the resting mass of the oscillating portion of the probe cell 20. In turn, the resting mass of the probe cell 20 depends on the number of probe segments 35 in the sensing layer 34. For example, by anchoring 5000 strands/μm$^2$ each having a length of 25 bases (25 bp), considering that each DNA segment has a mass of about $1.38 \times 10^{-20}$ g, with a sensing area diameter of 100 μm, the mass before hybridization is about $5.4 \times 10^{-13}$ g.

Assuming that the hybridization efficiency (number the target segments binding with the probe segments 35) is about 50% and that the target segments have 150-400 bp, the final mass of the probe cell 20 may be estimated to be about $1.6$-$4.3 \times 10^{-12}$ g.

In such a situation, a mass change Δm=1-4 picograms for each probe cell 20 is obtained.

When target DNA binds with the probe segments 35, the resonator undergoes an oscillation frequency variation Δf, according to equation (1).

Assuming a noise at 27 Hz, from theoretical considerations it follows that the resolution of the probe cell 20 is about 0.5 picograms. Therefore, a device including of even only four probe cells 20 is able to detect any hybridization.

The probe cell 20 has a very high sensitivity, due its small area. Furthermore, it may be manufactured using manufacturing steps typical of semiconductor integrated devices, and thus, at low cost, allowing its use in a number of applications.

The probe cell 20 may be manufactured using basically the processes taught in EP-A-1324382 for forming an SOI wafer and in EP-A-1577656 for forming a pressure sensor.

Figure 4:
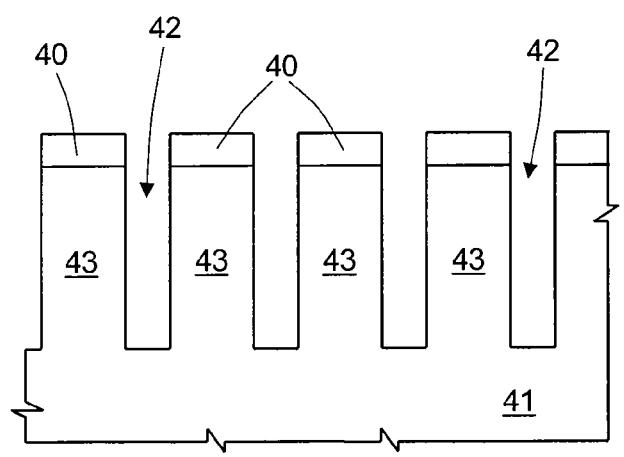
FIG. 4 shows an enlarged, cross-sectional view of a semiconductor substrate, in a manufacturing step of the device of FIG. 3.
Figure 5:
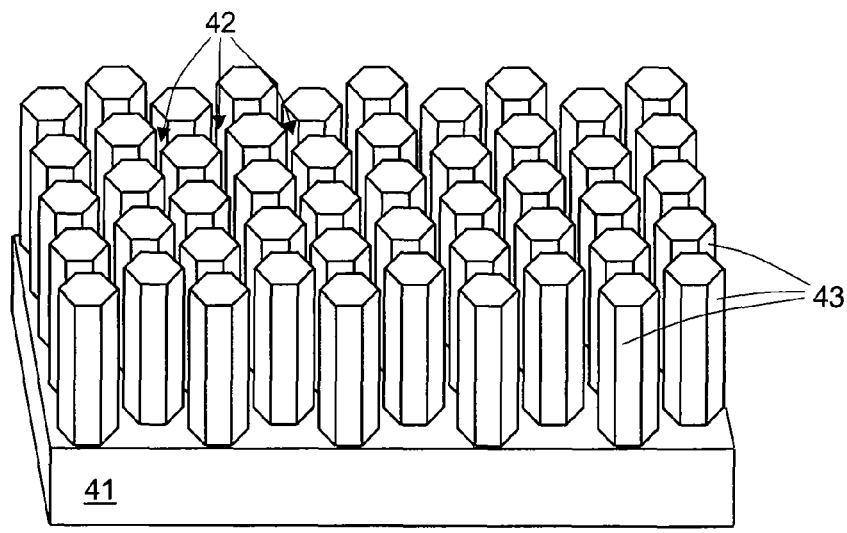
FIG. 5 is a prospective view of the structure of FIG. 4.

In detail and as shown in FIG. 4, a mask 40, is laid on a substrate 41 of semiconductor material, for example silicon, which is anisotropically dry etched to form a plurality of trenches 42 having a width, e.g., of 1 μm, communicating with each other and delimiting a plurality of columns 43 having an essentially hexagonal section, as visible from FIG. 5. For example, the trenches 42 may have a height of 11 μm±1 μm and the columns 43 may have a diameter of 2 μm.

Then, epitaxial growth is carried out as described in the above cited patents. As a consequence, an epitaxial layer 44 grows on the columns 43 and upwardly closes the trenches 42.

Thereafter, a thermal annealing is performed, for example for 25-30 minutes at about 1200° C., preferably in hydrogen atmosphere. As an alternative, nitrogen can be used, by employing longer times and suitable protection layers.

Figure 6:
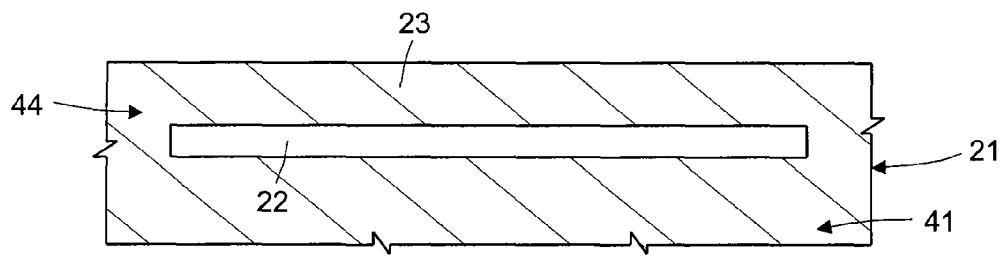
FIG. 6 shows an enlarged, cross-sectional view of the substrate of FIG. 4, in a subsequent manufacturing step.

As discussed in the above cited patent applications, annealing causes a migration of the silicon atoms toward a lower energy configuration. As a consequence, by suitably selecting the width of the trenches 42, it is possible to cause a complete migration of the silicon atoms away from the columns 43, resulting in the formation of the buried cavity 22, as shown FIG. 6. Over the buried cavity 22, a silicon layer forming the diaphragm 23 is obtained, having a thickness of, e.g., 20 μm, formed in part by epitaxially grown silicon atoms and in part by migrated silicon atoms. Thereby, body 21 is obtained.

On a wafer so obtained, the electronic components of the oscillator and any other electronic circuits associated thereto may be integrated. Thus, in one example, buffer layer 25 is deposited, preferably by RF sputtering. Buffer layer 25, for example of AlN, has the aim of optimizing the quality of the molybdenum layer forming the bottom electrode 26 and, as a consequence, helping the subsequent growth of the piezoelectric layer intended to form piezoelectric regions 27. Buffer layer 25 can be left on the whole wafer surface, at least in the probe area, or can be defined to form a buffer region 25 extending only under the piezoelectric region 27.

Then, a first electrode layer 26 is deposited, e.g. molybdenum. The use of molybdenum has proven particularly advantageous for the performance of the probe cell 20. In fact, the piezoelectric effect of a given piezoelectric layer depends on the orientation quality of the piezoelectric layer along the crystallographic axis, perpendicularly to the growth plane. Piezoelectric polycrystalline layers having a high orientation degree have piezoelectric properties that are similar to an epitaxial layer, with the advantage that they can be deposited at lower temperatures. Studies by the applicant have shown that molybdenum is more efficient than aluminum in causing the formation of highly oriented piezoelectric layers of AlN, thus the use of the molybdenum and AlN helps to obtain high sensitivity of the probe cell 20.

The first electrode layer 26 may cover the entire wafer surface, at least in the probe area, since it forms a ground electrode, common to all the probe cells 20, and may be used as a metal level for the associated circuitry, connected to standard aluminum tracks.

Thereafter, a piezoelectric layer, preferably AlN, is sputtered and defined, so as to obtain the piezoelectric region 27. In the alternative, the piezoelectric layer may be left in the probe area of the chip, so as to avoid the presence of a step during the subsequent deposition of the upper electrode layer 30. After depositing the upper electrode layer 30, preferably molybdenum, the latter is defined using known photolithographic steps, so as to form the upper electrode 30.

In the alternative to the above, it is possible to define the upper and lower electrode layers 30, 26 and the piezoelectric layer 27 in sequence, only after depositing the upper electrode layer 30.

Then, the bond region 33, e.g. of NiPdAu, is deposited on the upper electrode 30 and defined; the protection layer 37, such as nitride, is deposited on the entire surface of the wafer and removed from the areas where the sensing region 34 and the pads are to be formed.

The wafer is diced to obtain a plurality of dice and the associated circuitry (indicated generally at 38); then the wires 28, 31, e.g. Au, are bonded, and shielded, e.g. by growing a protection layer of non-conductive plastics (e.g. the plastic known as "glob top"). Finally, the sensing layer 34 is deposited, e.g., by spotting.

Figure 7:
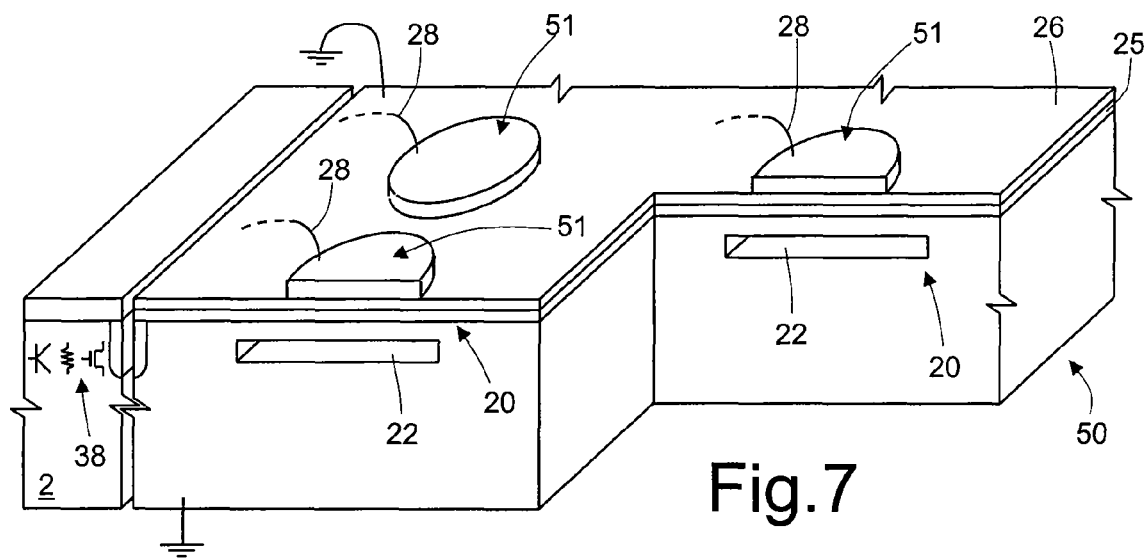
FIG. 7 is a prospective, partly broken view of an array of probes according to FIG. 3.

A plurality of probe cells 20 can be integrated in the same chip in an array. FIG. 7 shows an embodiment including a chip 50 integrating a plurality of probe cells 20, for example 6×21 probe cells 20 (only three whereof are visible). The probe cells 20 have the structure shown in FIG. 3 and are represented schematically herein, wherein number 51 identifies the piezoelectric and sensing portion. In this embodiment, the bottom electrode 26 covers the entire surface of the probe cells 20. In the alternative, the bottom electrode layer 26 may be defined in order to form pads and interconnection lines toward the associated internal and external circuitry (FIG. 8).

The chip 50 is manufactured as discussed above. In particular, the trenches 42 are patterned so as to obtain a plurality of cavities 22, the bottom electrode 26 and the piezoelectric region 27 may be common to all the probe cells 20 or may be defined to form a plurality of regions 26, 27, as shown in FIG. 7, and the final chip comprises a plurality of probe cells 20.

In use, the resonant frequency of each probe cell 20, after functionalization of the electrodes and before hybridization, is measured. Then after exposing the probe cells 20 to the fluid that has to be analyzed, the resonant frequency of each probe cell 20 is measured again and compared with the previous value: hybridization has occurred if the resonance frequency has changed. In this way the presence of DNA fragments complementary to the probes in the sample mixture can be detected and quantified.

Figure 8:
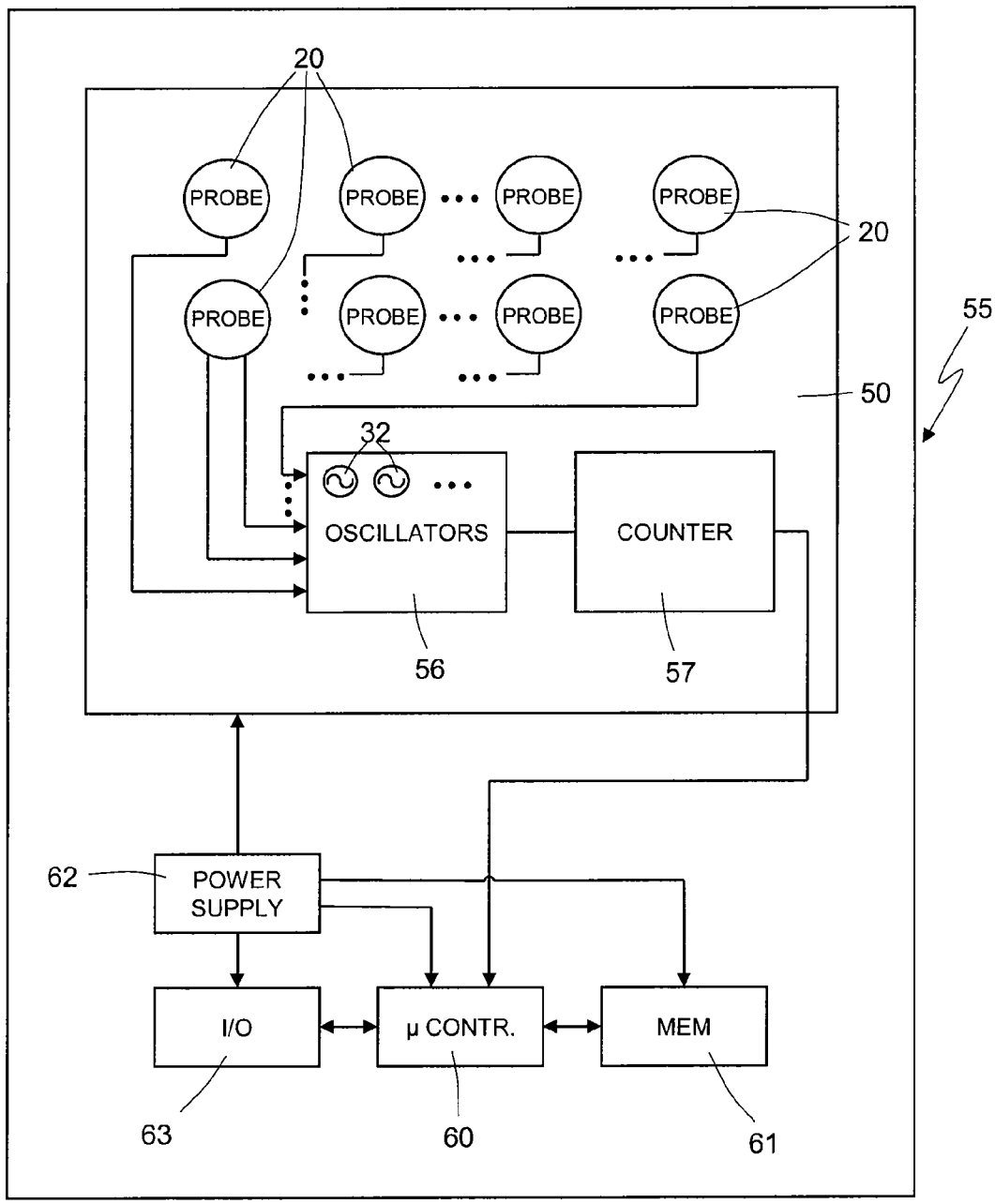
FIG. 8 is a simplified block diagram of a hybridization detecting unit according to an embodiment of the invention.

FIG. 8 shows a hybridization detection unit 55 comprising a board 58 supporting the chip 50. The chip 50 integrates an array of probe cells 20, and an associated electronics, including an oscillator stage 56, having a plurality of oscillators 32, one for each probe cell 20, and a converter 57, for example a counter. The oscillator stage 56 drives the array of probe cells 20 and generates a plurality of periodical signals (pulse trains) having rest frequencies f1, f2, ..., fn of the resonators 32; the counter 57 counts the number N of pulses for each signal within a fixed time T and generates digital signals codifying their oscillation frequencies f, whose value depends on whether the probe segments 35 have bound with the respective analytes.

The output of the chip 50 is connected to a microcontroller 60 in turn connected to a memory 61, for example an EEPROM, to a power supply 62 and to an input/output stage 63. The microcontroller 60 is thus able to detect any frequency difference Δf for each probe cell 20 and, thus, hybridization thereof.

If the single probe cells 20 are functionalized with different probe fragments 35, and using patterns stored in the memory 61, it is possible to detect the presence of complex analytes, having sequences able to bind with the different probe fragments. With probes of sufficient complexity, it will even be possible to determine the sequence of the target molecule by assembling the hybridization data to provide a complete sequence.

In the alternative, if all the probe cells 20 have been functionalized with the same probe segments, it is possible to detect extremely low-concentrations of analyte.

Figure 9:
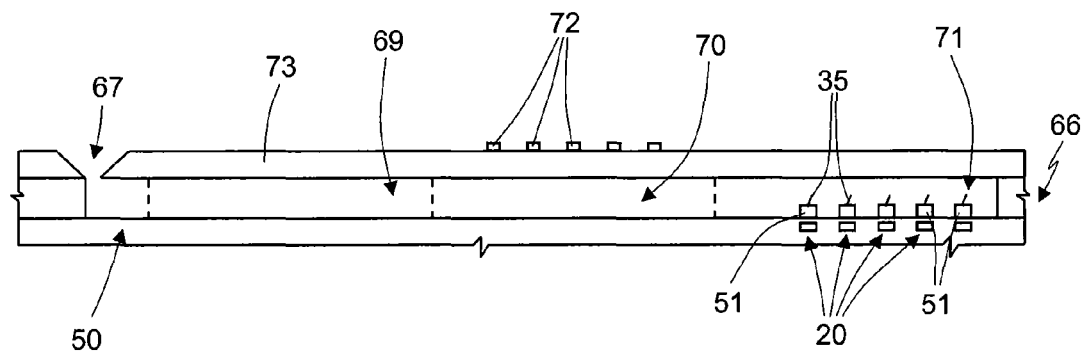
FIG. 9 is a simplified cross-section of a chip integrating an embodiment of the instant detecting device.
Figure 10:
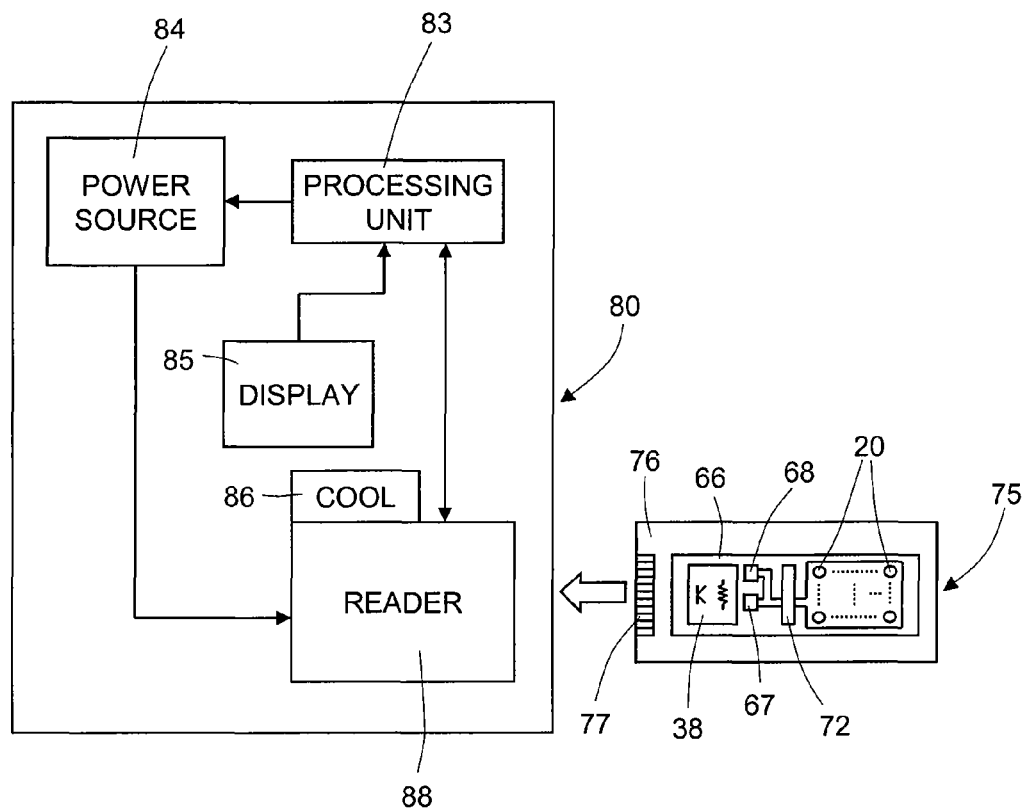
FIG. 10 is a simplified block diagram of a hybridization detecting apparatus using the chip of FIG. 9.

According to another embodiment, FIGS. 9 and 10, the array of probe cells 20 and the associated circuitry 38 form an integrated microfluidic device 66 comprising a sample reservoir 67, a reagents reservoir 68 (FIG. 10), a sample preparation channel 69, an amplification chamber 70, and a detection chamber 71, all in fluidic connection.

The microfluidic device 66 is also provided with a micropump, here not illustrated, for moving the biological sample and reagents from the reservoirs 67, 68 toward the detection chamber 71, e.g. arranged downstream.

The sample reservoir 67 and the reagent reservoir 68 are opened on a surface of the microfluidic device 66, so as to be accessible from the outside.

The sample preparation channel 69 may comprise a dielectrophoretic cell and lysis chamber (not shown), for separating nucleated cells of the biological sample from non-nucleated cells and filtering out the non-nucleated cells.

Heaters 72 may be arranged on the surface of the microfluidic device 66 and may be driven by a control unit (e.g. processing unit 83 in FIG. 10), in order to heat and cool the amplification chamber 70 according to a predetermined temperature profile (thermocycling).

The detection chamber 71 can accommodate an array of probe cells 20, e.g. as shown in FIG. 7.

The microfluidic device 66 may be upwardly closed by a plate 73 (e.g. a glass sheet), bonded onto the chip 50.

In one application of the device, particular nucleic acid sequences can be detected using oligonucleotide probes. A sample of raw biological material (e.g. blood) is introduced in the sample reservoir 67 and is moved to the sample preparation channel 69. After separation of nucleated cells (e.g., white blood cells), the biological sample is combined with reagents for lysis and PCR, which are supplied by the reagent reservoirs 68. Then, the biological sample and the reagents are mixed, the nuclei of the cells are chemically broken and the DNA is extracted. The DNA is thermally denatured and amplified in the amplification chamber 70 and, finally, the processed biological sample is supplied to the detection chamber 71, for hybridization of target nucleotide sequences and detection thereof, as previously discussed.

According to FIG. 10, the microfluidic device 66 is mounted on a cartridge 75 intended to be loaded into a biochemical analysis apparatus 80. The apparatus 80 comprises the processing unit 83, a power source 84 controlled by the processing unit 83, a display 85, a reader 88 and a cooling unit 86. The cartridge 75 comprises a board 76 supporting the microfluidic device 66 and an interface 77 and may be removably inserted in the reader 88, for selective coupling to the processing unit 83 and to the power source 84. The heaters 72 are coupled to the power source 84 through the interface 77. In the alternative, the heaters 72 may be provided on the board 76 or integrated into the reader 88. The cooling unity 86 may be a Peltier module or a fan coil, controlled by the processing unit 83 and thermally coupled to the cartridge 75 when loaded in the reader 88.

The advantages of the present hybridization detection device are clear from the above.

In particular, the present device has high sensitivity, thanks to its integration in a semiconductor chip of reduced dimensions, and to the use of molybdenum in contact with the piezoelectric region 27.

The formation of the diaphragm 23 above the buried cavity 22 allows manufacturing the probe cell 20 using simple and cheap techniques, thereby has low overall manufacturing costs. In fact, forming the diaphragm with the described technique allows obtaining a uniform and well controllable thickness for an oscillating mass.

The definition of the diaphragm 23 through the buried cavity 22 allows a simple and precise control of the thickness of the diaphragm 23, in addition to the thickness of the overlying layers, without the need of specific and/or expensive calibration of the oscillation frequency.

The definition of the diaphragm 23 through the buried cavity 22 results in the entire probe cell 20 having substantially the same area as the piezoelectric and sensing portion 51. As a consequence, each probe cell 20 has reduced area, allowing the integration of a plurality of probe cells 20 in the same chip, thus using the same associated driving and control stages.

Finally, it is clear that numerous variations and modifications may be made to the detection device described and illustrated herein, all falling within the scope of the invention as defined in the attached claims.

For example, part of the electronic components processing the electronic signals generated by the converter 57 can be integrated in the same chip as the probe cells, if so desired and possible in view of the used temperatures.

Additionally, the sensor has been exemplified herein using DNA probes bound to the sensor via a biotin streptavidin interaction. However, there are many linkers and/or chemistries available for selective binding of oligonucleotide probes to substrates, which are not detailed herein (see, e.g., Immobilisation of DNA on Chips II in Topics in Current Chemistry, Volume 261 (2005), Microarrays (Humana Press, 2007)).

Further, the sensor can also be applied to the detection of other biological molecules. For example, the probes might be antibodies, which can be selectively deposited by known linkers and/or chemistries (see e.g., Protein Microarray Technology (Wiley-VCH 2004), Protein Arrays, Biochips and Proteomics (CRC 2003), Protein Microarrays (Jones & Bartlett Publishers, 2005) or via the well known and exemplified biotin streptavidin conjugates. With an antibody probe, an infinite number of peptides, proteins, lipids, carbohydrates and the like can thus be detected. The probe can also be a ligand (e.g., a steroid), a receptor or other protein, a substrate for a protein, an aptamer, or any other molecule with high affinity for the analyte of interest.

Figure 11:
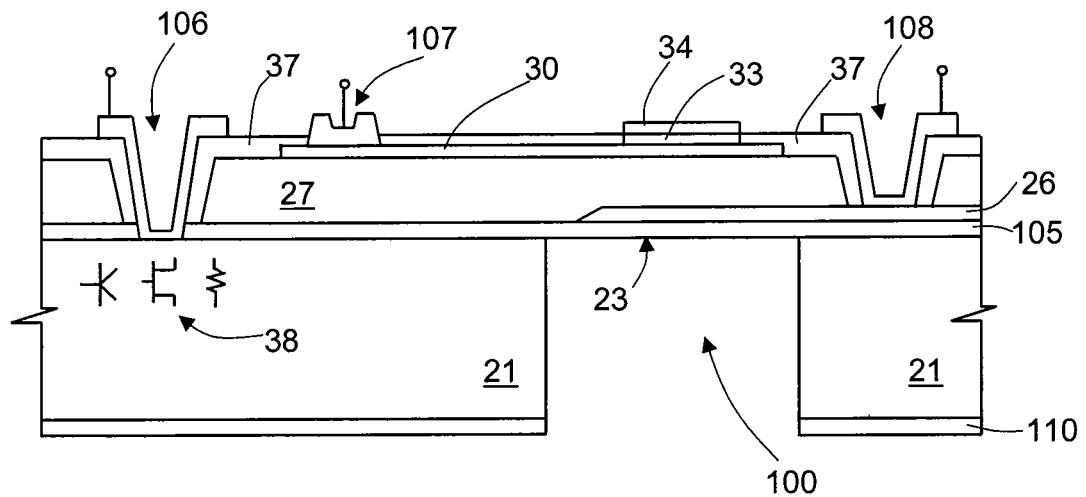
FIGS. 11-13 are different embodiments of the instant detection device.

FIG. 11 shows an embodiment of the present detector wherein the cavity underlying the diaphragm is not buried. In detail, here the substrate 21 has a trench 100 obtained using the technique of bulk micromachining by selectively removing a portion of the silicon substrate 21 from the back using a reactive ion etching plasma tool. A dielectric layer 105, e.g., thermally grown silicon dioxide, extends on the surface of the substrate 21 and defines the diaphragm 23. A circuitry 38 extends laterally to the detection area; contacts 106-108 connect the circuitry 38, the bottom electrode 26 and the upper electrode 30 to the other components of the detecting device, e.g. the detection unit 55 of FIG. 8. Here, the substrate 21 is a standard substrate having a thickness of 725 μm and a thermal oxide 110 having a thickness of 1 μm extends on the bottom surface of the substrate 21.

The substrate 21 has here a trench 100 for each microbalance or probe cell 20.

Figure 12:
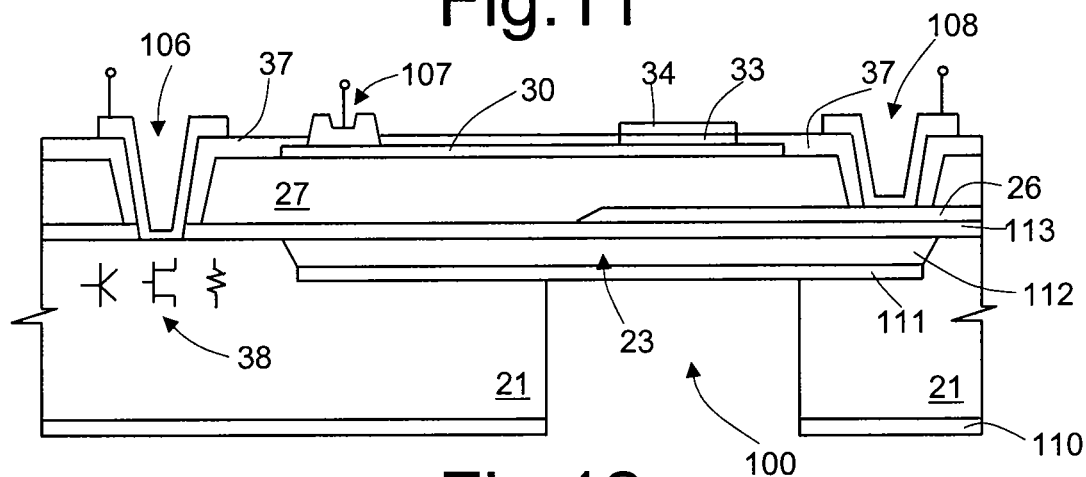

In FIG. 12, the diaphragm 23 is formed by a multilayer including a bottom dielectric region 111 (e.g., of silicon dioxide), a polysilicon portion 112 and an upper dielectric layer 113 (e.g., of silicon dioxide). Such a structure may be obtained, before forming the components of the circuitry 38, during the epitaxial growth. In detail, before growing an epitaxial layer, the bottom dielectric region 111 is thermally grown or deposited on the sensing portions of the wafer, so that during the epitaxial growth, the polysilicon portion 112 grows over the bottom dielectric region 111. Elsewhere, the epitaxial layer is monocrystalline, to allow integration of electric components. Then, after the integration of the circuitry 38, the upper dielectric layer 113 is grown or deposited and covers the entire surface of the substrate 21. In the alternative, the bottom dielectric region 111 and the polysilicon portion 112 may be grown or deposited on the upper surface of the substrate 21, before or after forming the components of the circuitry 38.

Figure 13:
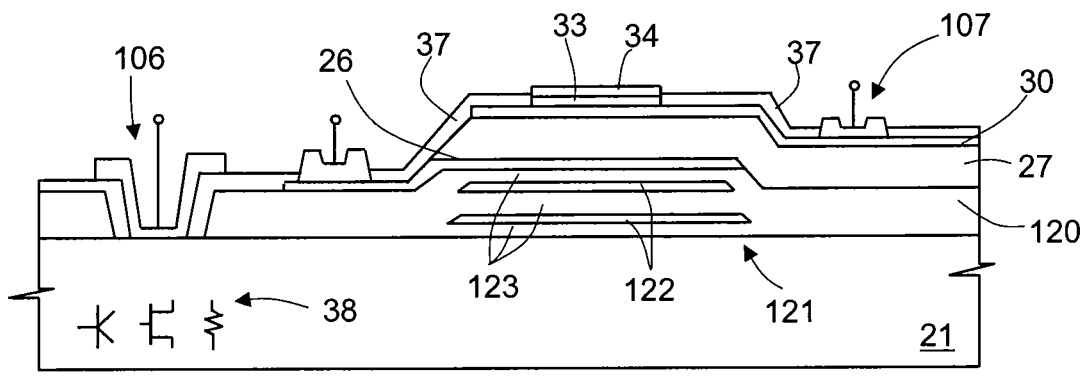

FIG. 13 is an embodiment wherein the detecting device uses the reflecting ability of a Bragg mirror to contain the acoustic waves in the overlying piezoelectric region 27 and thus is functionally equivalent to the buried cavity 3 or the trench 100. In detail, here, the substrate 21 is covered by a thick dielectric layer 120 which, in a sensor portion thereof, accommodates a mirror 121. The mirror 121 is formed by a stack of alternating high acoustic impedance layers 122 and low acoustic impedance layers 123 as described, e.g., in U.S. Pat. Nos. 6,448,695 or 6,933,807. As an example, the low acoustic impedance layers 123 may be of silicon dioxide and the high acoustic impedance layers 122 may be wolfram (tungsten).

Figure 14A:
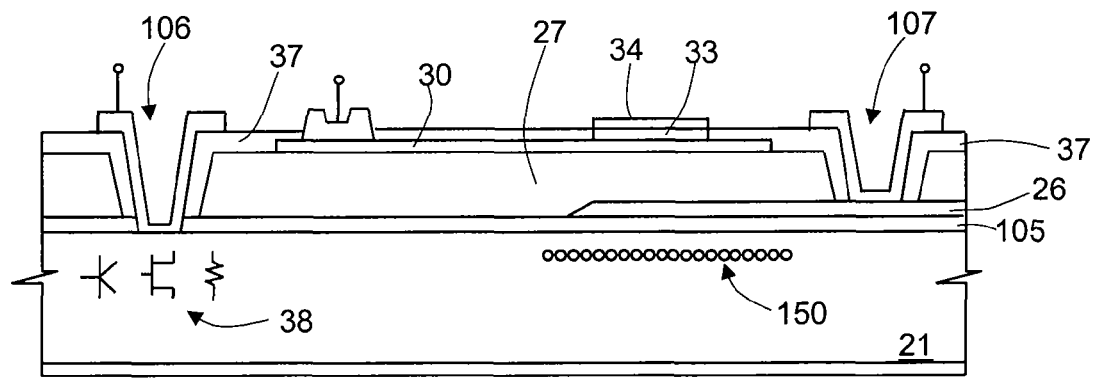
FIGS. 14a and 14b show a different embodiment of the present detection device, in two subsequent manufacturing steps.
Figure 14B:
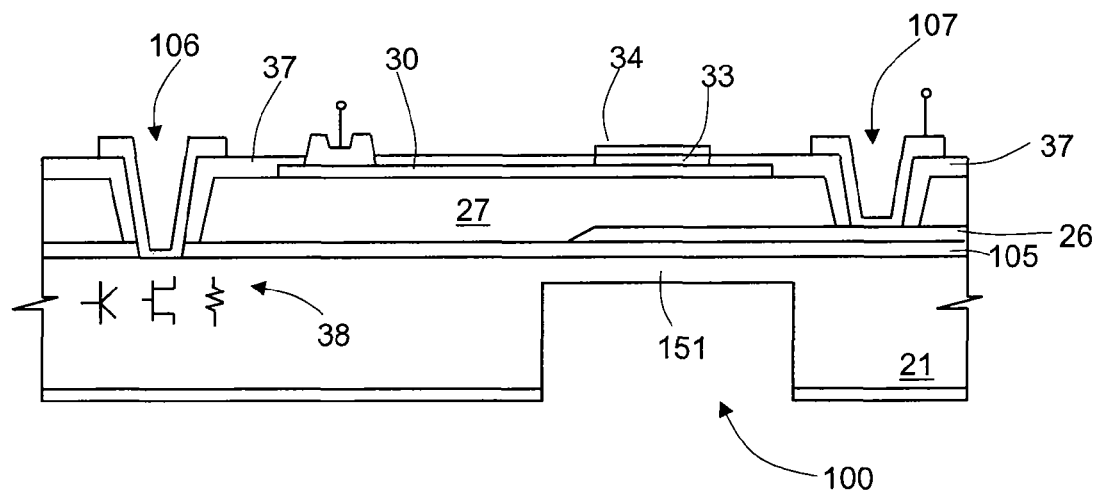

FIGS. 14a and 14b refer to an embodiment wherein the cavity 100 is not obtained by bulk micromachining, but by using the process described in U.S. Pat. Nos. 7,294,536 or in 7,071,073. In particular, before forming the components of the circuitry 38, a buried oxide layer 150 is formed in the substrate 21, FIG. 14a. At the end of the process, after forming the circuitry and the detector regions 25-27, 30, 33, 34 and 37 on the surface of the substrate 21, the substrate 21 is etched from the back to selectively remove silicon until reaching the buried oxide layer 150. The buried oxide layer 150 is removed as well, forming the cavity 100 under a silicon layer 151 under the substrate upper surface which forms a diaphragm 152. Here, the substrate 21 may have a thickness of 308 μm.

What is claimed is:

1. A hybridization detecting device, comprising:
a body made of a semiconductor material;
an electronic high-frequency circuit integrated in the body;
a probe cell arranged laterally to the electronic high-frequency circuit, the probe cell including a diaphragm made of said semiconductor material, a first electrode on the diaphragm, a piezoelectric region on the first electrode, a second electrode on the piezoelectric region and a detection layer on the second electrode, wherein said semiconductor material is monocrystalline silicon.

2. A device according to claim 1, wherein the body accommodates a buried cavity arranged underneath and delimiting a bottom surface of the diaphragm, the diaphragm being a portion of the body.

3. A device according to claim 1, wherein the body has a back surface and accommodates a trench extending from the back surface and delimiting the diaphragm.

4. A device according to claim 1, wherein the diaphragm is delimited by a Bragg mirror, including a stack of high and low acoustic impedance layers.

5. A device according to claim 1, wherein the first electrode is of molybdenum.

6. A device according to claim 1, wherein the second electrode is of molybdenum.

7. A device according to claim 1, wherein the circuit comprises an oscillating circuit connected to the piezoelectric region through the first and second electrodes, the oscillating circuit forming, together with the piezoelectric region, a resonant circuit.

8. A device according to claim 1, further comprising a buffer layer extending between the body and the first electrode.

9. A device according to claim 8, wherein the piezoelectric region and the buffer layer are of aluminum nitride.

10. A device according to claim 1, wherein the detection layer comprises an oligonucleotide or an antibody.

11. A device according to claim 1, comprising a plurality of probe cells, wherein the body accommodates a plurality of distinct cavities underlying each of a respective plurality of piezoelectric regions.

12. A microfluidic device comprising a body made of a semiconductor material, the body accommodating:
- a plurality of probe cells, each probe cell including a diaphragm made of said semiconductor material, wherein said semiconductor material is monocrystalline silicon,
- a first electrode on the diaphragm, a piezoelectric region on the first electrode, a second electrode on the piezoelectric region and a detection layer on the second electrode;
- an electronic high-frequency circuit;
- a sample reservoir;
- a reagents reservoir;
- a sample preparation channel;
- an amplification chamber, and
- a detection chamber,
- the sample reservoir, the reagents reservoir, the sample preparation channel, the amplification chamber and the detection chamber being in mutual fluidic connection.

13. A process for manufacturing a hybridization detecting device, comprising:
- providing a wafer of a semiconductor material having a surface;
- integrating an electronic circuit in the wafer;
- forming a diaphragm laterally to the electronic circuit and of the same semiconductor material as said wafer, wherein said semiconductor material is monocrystalline silicon,
- forming a first electrode on the diaphragm,
- forming a piezoelectric region on the first electrode,
- forming a second electrode on the piezoelectric region, and
- forming a detection layer on the second electrode.

14. A process according to claim 13, wherein at least one electrode of the first and the second electrode is of molybdenum.

15. A process according to claim 13, further comprising forming an oscillating circuit within the body and connecting the oscillating circuit to the piezoelectric region.

16. A process according to claim 13, further comprising forming a buffer layer on the body, below the first electrode; the piezoelectric region and the buffer layer being of aluminum nitride.

17. A process according to claims 13, wherein the detection layer comprises an oligonucleotide, an antibody, purified proteins peptides, allergens.

18. A process according to claim 13, wherein forming a diaphragm comprises forming a buried channel in the body.

19. A process according to claim 13, wherein forming a diaphragm comprises forming, under the first electrode, a Bragg mirror including a stack of high and low acoustic impedance layers.

20. A hybridization detecting device, comprising:
- a body made of a monocrystalline silicon;
- an electronic high-frequency circuit integrated in the body;
- a probe cell arranged laterally to the electronic high-frequency circuit, the probe cell including a diaphragm made of said monocrystalline silicon, a first electrode on the diaphragm, a piezoelectric region on the first electrode, a second electrode on the piezoelectric region and a detection layer on the second electrode,
- wherein the body accommodates a buried cavity arranged underneath and delimiting a bottom surface of the diaphragm, the diaphragm being a portion of the body.

* * * * *